(12) United States Patent
Mebatsion (10) Patent No.: US 6,887,479 B2
(45) Date of Patent: May 3, 2005

(54) ATTENUATED RECOMBINANT RABIES VIRUS MUTANTS AND LIVE VACCINES THEREOF

(75) Inventor: Teshome Mebatsion, Boxmeer (NL)

(73) Assignee: Akzo Nobel N.V., Arnhem (NL)

( * ) Notice: Subject to any disclaimer, the term of this patent is extended or adjusted under 35 U.S.C. 154(b) by 0 days.

(21) Appl. No.: 10/128,628

(22) Filed: Apr. 23, 2002

(65) Prior Publication Data

US 2002/0164356 A1 Nov. 7, 2002

(30) Foreign Application Priority Data

Apr. 23, 2001 (EP) .............................................. 01201464
Oct. 5, 2001 (EP) .............................................. 01203773

(51) Int. Cl.$^7$ .......................... A61K 39/12; C12N 7/04; C07H 21/04
(52) U.S. Cl. ................................ 424/224.1; 424/199.1; 424/204.1; 435/236; 536/23.5; 536/23.72
(58) Field of Search ........................... 424/199.1, 202.1, 424/204.1, 205.1, 224.1; 536/23.1, 23.5, 23.72; 435/236, 237, 238, 239

(56) References Cited

FOREIGN PATENT DOCUMENTS

| WO | 00/32755 | | 6/2000 |
|---|---|---|---|
| WO | WO 00/32755 | * | 6/2000 |

OTHER PUBLICATIONS

Dietzschold et al. Rhabdoviruses. In B.N. Fields et al. (ed.), Fields Virology, 3rd ed. Philadelphia: Lippencott–Raven Publishers 1996: 1144.*
Wild et al. Journal of General Virology. 1981; 57: 169–177.*
Jacob et al. Journal of Virology. Nov., 2000; 74(21): 10217–10222.*
Mebatsion et al. (PNAS. 1996; 93: 7310–7314.*
Schnell M J et al: Infectious Rabies Viruses From Cloned CDNA: EMBO Journal, Oxford University Press, Surrey, GB, vol. 13, No. 18, Sep. 1, 1994 pp. 4195–4203.
Raux Helene et al: "Interaction of the rabies virus P protein with the LC8 dynein light chain.", Journal of Virology, vol. 74, No. 21, Nov. 2000, pp. 10212–10216.
Jacob Yves et al: "Cytoplasmic dynein LC8 1–7, 9–14 interacts with lyssavirus phosphoprotein.", Journal of Virology, vol. 74, No. 21, Nov. 2000, pp. 10217–10222.
Mebatsion et al: "Highly stable expression of a foreing gene from rabies virus vectors", Proceedings of the National Academy of Sciences of USA, Washington, US, vol. 93, Jul. 1996, pp. 7310–7314.
Jacob Yves et al: "Functional interaction map of lyssavirus phosphoprotein: Identification of the minimal transcription domains.", Journal of Virology, vol. 75, No. 20, Oct. 2001, pp. 9613–9622.
Mebatsion Teshome: "Extensive attenuation of rabies virus by simultaneously modifying the dynein light chain binding site in the P protein and replacing Arg333 in the G protein.", Journal of Virology, vol. 75, No. 23, Dec. 2001, pp. 11496–11502.

* cited by examiner

Primary Examiner—Shannon Foley
(74) Attorney, Agent, or Firm—William P. Ramey, III (57) ABSTRACT

The present invention describes recombinant RV mutants comprising a combine mutation in two different parts of the viral genome, involving the P and the G genes. The mutations in the P gene preferably encompass residues 139 to 170, more preferably residue 139 to 149, most preferably residues 143–149. The mutation can be a substitution or deletion of one or more amino acids in the above region, as well as combinations of deletion and substitution.

18 Claims, 8 Drawing Sheets

Infectious titer (log₁₀/ml) of rabies virus mutants

Pathogenicity of rabies virus mutants to day-old suckling mice after intramuscular inoculation

| | 7 days pi | 10 days pi | 15 days pi | 21 days pi | 7 days pi | 10 days pi | 15 days pi | 21 days pi |
|---|---|---|---|---|---|---|---|---|
| ■ SAD-D29 | 0 | 100 | 100 | 100 | 0 | 100 | 100 | 100 |
| ☐ D29-d7 | 0 | 83 | 100 | 100 | 0 | 0 | 17 | 17 |
| ■ D29-d11 | 0 | 50 | 83 | 83 | 0 | 0 | 0 | 0 |

Dose: 100,000 ffu/mice     100 ffu/mic

SEQUENCE LISTING

<160> NUMBER OF SEQ ID NOS: 4

<210> SEQ ID NO 1
<211> LENGTH: 30
<212> TYPE: DNA
<213> ORGANISM: Rabies virus

<400> SEQUENCE: 1
cttgagctct cggcctcctg gagggttggg                              30

<210> SEQ ID NO 2
<211> LENGTH: 30
<212> TYPE: DNA
<213> ORGANISM: Rabies virus

<400> SEQUENCE: 2
cttgagctct cggccctctg aagactttcc                              30

-continued

```
<210> SEQ ID NO 3
<211> LENGTH: 30
<212> TYPE: DNA
<213> ORGANISM: Rabies virus

<400> SEQUENCE: 3
cccaaccctc caggaggccg agagctcaag                                    30

<210> SEQ ID NO 4
<211> LENGTH: 30
<212> TYPE: DNA
<213> ORGANISM: Rabies virus

<400> SEQUENCE: 4
ggaaagtctt cagagggccg agagctcaag                                    30
```

ATTENUATED RECOMBINANT RABIES VIRUS MUTANTS AND LIVE VACCINES THEREOF

RELATED APPLICATIONS

This application claims priority from European patent application number 01201464.3 filed on Apr. 23, 2001 and European patent application number 01203773.5 filed on Oct. 5, 2001.

FIELD OF THE INVENTION

The present invention is related to attenuated rabies virus mutants comprising combined attenuating mutations in their glycoprotein and phosphoprotein genes.

The present invention is related to attenuated rabies virus mutants comprising combined attenuating mutations in their glycoprotein and phosphoprotein genes.

Rabies remains one of the most dreadful infectious diseases affecting human and animals, despite significant scientific advances in its prevention and control. Rabies presents as a distinct problem in different parts of the world. In the more industrialized nations, the risk to human beings has minimized significantly, mainly due to mandatory vaccination programs of dogs and other pet animals. Although wild life rabies still exists in the developed countries, most impressive progress has been made in control and elimination of wildlife rabies using oral immunization of wild carnivores.

In contrast, rabies remains a major threat to public health and persists to cause numerous human deaths in the less industrialized nations. Dog rabies is still epizootic in most countries of Africa, Asia and South America and in these countries dogs are responsible for most human deaths from the disease. Therefore, introducing new control strategies in addition to the existing parenteral vaccination programs is a necessity. Due to the success in control of wildlife rabies, several developing countries are presently volunteering to make use of oral vaccination of dogs.

For the purpose of oral immunization of dogs, the vaccine should be highly safe due to very close contact between dogs and humans than between wild animals and humans. Therefore, there is an ongoing need for safe attenuated live rabies vaccines, which do not have residual pathogenicity or the potential to revert to the pathogenic variant.

Rabies virus (RV) is a non-segmented negative-stranded RNA virus of the Rhabdoviridae family. RV is composed of two major structural components: a nucleocapsid or ribonucleoprotein (RNP), and an envelope in the form of a bilayer membrane surrounding the RNP core. The infectious component of all Rhabdoviruses is the RNP core which consists of the RNA genome encapsidated by the nucleoprotein (N) in combination with two other proteins, i.e. RNA-dependent RNA-polymerase (L) and phosphoprotein (P). The membrane surrounding the RNP core consists of two proteins: a trans-membrane glycoprotein (G) and a matrix (M) protein located at the inner site of the membrane.

The G protein, also referred to as spike protein, is responsible for cell attachment and membrane fusion in RV and additionally is the main target for the host immune system. The amino acid region at position 330 to 340 (referred to as antigenic site III) of the G protein has been identified to be responsible for the virulence of the virus, in particular the Arg residue at position 333.

Currently available attenuated live anti-rabies vaccines are based on attenuated RV vaccine strains including the SAD Bern strain or the SAD B19 strain, however these vaccines still have undesired residual pathogenicity. Several attempts have been made to obtain non-pathogenic RV strains for use in a live vaccine. European Patent 350398 describes an avirulent RV mutant SAG1 derived from the Bern SAD strain of RV in which the glycoprotein possesses Ser instead of Arg at position 333. The avirulent mutant SAG1 was obtained under selection pressure of specific monoclonal antibodies on the SAD Bern strain. In adult mice SAG1 has been found to be non-pathogenic. However, pathogenic revertants of the attenuated virus occurred at a frequency of 1 in 10,000 (Lafay et al, Vaccine 12. pp. 317–320, 1994). The genetic instability of this mutant renders it unsuitable for safe vaccination.

European patent application 583998 describes another attenuated RV mutant, SAG2, in which Arg at position 333 has been substituted by Glu in the glycoprotein. SAG2 is non-pathogenic for adult mice when administered by various routes. Because this mutant also has the potential to revert to the pathogenic parenteral strain, the vaccine is produced in the presence of specific monoclonal antibodies to prevent reversion (Blancou and Meslin, 1996; In Laboratory techniques in rabies, pp. 324–337). Since these specific monoclonal antibodies are not present in inoculated animals, vaccination with such mutant still has the risk that the mutant reverts to virulence in the inoculated animal resulting in disease outbreaks in the inoculated animals and possible spread of the pathogen to other animals.

Furthermore, stable attenuated RV mutants were described in WO00/32755, the contents of which are herewith incorporated by reference, which possess replacements of the Arg at position 333 of the G protein with other amino acids that differs by all three nucleotides from the $Arg_{333}$ codon in the parent virus.

All the above described live rabies vaccine viruses possessing an amino acid differing from Arg at position 333 of the glycoprotein are non-pathogenic to immune-competent adult mice. However, they are still pathogenic when inoculated to 1–2 day-old suckling mice, demonstrating the existence of residual pathogenicity and the risk associated with it for immune-deficient animals or humans.

SUMMARY OF THE INVENTION

The present invention has elegantly solved this problem by generating rabies virus mutants, which have a reduced pathogenicity for suckling mece.

The present invention describes recombinant RV mutants comprising a combined mutation in two different parts of the viral genome, involving the P and the G genes. The mutations in the P gene preferably encompass residues 139 to 170, more preferably residues 139 to 149. The mutation can be a substitution or deletion of one or more amino acids in the above region, as well as combinations of deletion and substitution.

Rabies virus P residues 138 to 172 have been mapped as domains responsible to bind to the LC8 dynein light chain (Raux et al., 2000, J. Virol. Vol. 74, pp. 10212–10216; Jacob et al., 2000, Vol. 74, pp. 10217–10222). It has been suggested that the interaction between P and LC8 might be important for rabies virus pathogenesis. However, a deletion of as much as 11 amino acids (residues 139–149) from this domain has no detectable effect upon the pathogenicity of a conventional rabies vaccine strain.

Surprisingly, when these mutations were introduced into rabies viruses lacking Arg at position 333 of their G protein, a dramatic reduction in pathogenicity for suckling mice was observed. This unexpected finding has a profound advantage in developing more safe live attenuated rabies vaccines.

DETAILED DESCRIPTION OF THE INVENTION

Preferred mutants according to the invention may be obtained by deleting residues 143 to 149 or 139 to 149 of the phosphoprotein (P) of rabies virus and simultaneously replacing the Arg at position 333 of the glycoprotein into another residue, preferably Asp instead of Arg.

The mutation in the G gene may comprise a mutation of the $Arg_{333}$ codon into a codon that differs by one, two or three nucleotides from said $Arg_{333}$ codon. Preferably the mutants are mutants of a RV strain in which all three nucleotides of the $Arg_{333}$ codon are substituted.

The mutants according to the invention are preferably mutants of RV strain SAD, especially RV strains SAD Bern and SAD B19. Preferred RV mutant according to the invention is a recombinant RV mutant in which the $Arg_{333}$ codon in the genome of RV strain SAD B19 has been substituted with a GAC triplet, coding for aspartic acid (Asp, D).

It was found that recombinant RV mutants possessing the combined mutation at the P and G genes are not pathogenic or much less pathogenic for 1–2 day-old suckling mice as opposed to single mutants containing only the described mutations on the P gene or the G gene. The introduction of the combined mutation into RV genome did not affect the growth rate of the virus in BSR cells and the final titer was similar to the parental strain. Furthermore, the introduced combined mutations did not affect the immunogenicity of the recombinant rabies viruses after oral administration into dogs. Similar levels of rabies-specific antibody titers were measured in dogs orally vaccinated with recombinant viruses possessing either only the G protein mutation or the combined mutations in P and G proteins. This makes the recombinant RV mutants according to the invention the safest live anti-rabies vaccines.

Such highly safe live rabies vaccine viruses can be used not only to immunize against rabies, but also as vaccine vectors to protect human and/or animals from other infectious agents. In addition to the other five viral proteins, rabies virus has been shown to express a foreign gene in a stable manner for more than 25 serial passages (Mebatsion et al., 1996; PNAS. Vol. 93, pp. 7310–7314). The potential of rabies virus based vectors as vaccines against other viral diseases such as HIV-1 was also demonstrated recently (Schnell et al., 2000; PNAS. Vol. 97, pp. 3544–3549). The introduction of the above described combined G and P protein mutations into rabies virus vectors will undoubtedly increase the safety of any rabies virus based vaccine vector.

The recombinant RV mutants according to the invention can be obtained using recombinant DNA technology and site-specific mutagenesis to introduce the desired mutations. Directed genetic manipulation of RV can be carried out using the reverse genetics system described in Schnell et al, 1994; EMBO J. Vol. 13, No. 18, pp. 4195–4203 and European patent application 0 702 085, both of which are hereby incorporated by reference. Site-specific mutagenesis can be carried out using commercially available kits.

An infectious full-length cDNA clone (pSAD-L16) of the vaccine strain SAD B19 described in Schnell et al., 1994 was used as a basis to introduce single or combined mutations in the P and/or G gene. RV mutants according to the invention can be obtained by a) introducing the desired mutation into the RV full-length cDNA clone, b) simultaneous expression of a full length antigenomic RV RNA from the modified cDNA and RV N, P, and L proteins from plasmids transfected into T7-RNA polymerase expressing cells, and 3) isolating the RV mutant viruses produced by said cells. The recombinant RV mutants according to the invention can be grown on a cell culture derived from for example BHK cells or human diploid cells. The viruses thus grown can be harvested by collecting the cell culture fluids and/or cells.

The vaccine according to the invention can be prepared using standard techniques available in the art. In general the vaccine is prepared by mixing the attenuated recombinant RV mutant according to the invention with a pharmaceutical acceptable carrier or diluent.

Pharmaceutical acceptable carriers or diluents that can be used to formulate a vaccine according to the invention are sterile and physiological compatible such as for example sterile water, saline, aqueous buffers such as alkali metal phosphates (e.g. PBS), alcohols, polyols, and the like. In addition the vaccine according to the invention may comprise other additives such as adjuvants, stabilisers, antioxidants, preservatives and the like.

Suitable adjuvants include but are not limited to aluminium salts or gels, carbomers, non-ionic blockcopolymers, tocopherols, monophospheryl lipid A, muramyl dipeptide, oil emulsions (w/o or o/w), cytokines, and saponins such as Quil A. The amount of adjuvant added depends on the nature of the adjuvant itself.

Suitable stabilisers for use in a vaccine according to the invention are for example carbohydrates including sorbitol, mannitol, starch, sucrose, dextrin, and glucose, proteins such as albumin or casein, and buffers like alkaline phosphates. Suitable preservatives include, amongst others, thimerosal, merthiolate, and gentamycin.

The attenuated live anti-rabies vaccine according to the invention can be administered to warm-blooded mammals, including humans, dogs, foxes, racoons and skunks via injection (intramuscularly, intradermally, or subcutaneously), spray or aerosol (intranasally), or per oral. Preferably the vaccine is administered to the subjects per oral, especially in case of wild life animals or stray-dogs. For oral administration the vaccine is mixed with a suitable carrier such as, for example, proteins or oils of vegetable or animal origin. For oral delivery, the vaccine formulation may further be encapsulated with baits prepared from metabolisable substances of animal or vegetable origin.

The useful dosage to be administered will vary, depending on the type of warm-blooded mammals to be vaccinated, the age, weight and mode of administration. In general a suitable dosage will vary between $10^2$ to $10^8$ $TCID_{50}$/mammal.

The following examples will illustrate the invention without limiting the invention thereto.

EXAMPLES

Example 1

Generation and Characterization of Recombinant Rabies Viruses with Modifications at the Dynein Light Chain Binding Site Materials and Methods Construction of cDNA clones: In order to introduce the desired mutations into the genome of rabies virus, a 2.2 kb BstB1 fragment comprising nucleotides 1497–3738 of rabies virus strain SAD B19 (nucleotide numbering is according to Conzelmann et al. 1990, Virology, Vol. 175, pp. 485–499; EMBL/GenBank accession No. M31046) was first cloned into pSK vector. Site directed mutagenesis was carried out using the "QuikChange Site-Directed Mutagenesis Kit" according to manufacturer's instructions. Primer pairs #142 and #143 (Table 1) were used to delete nucleotides at position 1940 to 1960, corresponding to amino acids 143 to 149 of rabies virus P protein. A larger deletion encompassing nucleotides 1928 to 1960, which corresponds to amino acids 139 to 149 of rabies virus P protein was also introduced using oligonucleotides #144 and 145 (Table 1). The accuracy of the introduced deletion was confirmed by sequencing the modified region. Clones containing the desired deletions (7 or 11 amino acids) were digested with NcoI and SnaBI and the respective ~0.8 kb fragments were used to replace the corresponding fragments of full length RV cDNA clones. The manipulation in pSAD-L16 (Schnell et al., 1994 EMBO J, Vol. 13, pp. 4195–4203), representing the SAD-B19 sequence gave rise to pL16-ΔP7 or pL16-ΔP11 (FIG. 1), possessing deletions of 7 or 11 residues, respectively. After a similar exchange of ~0.8 kb modified DNA fragments in pSAD-D29, a full-length clone possessing Asp (D) instead of Arg (R) at position 333 of the glycoprotein, two full-length clones—pD29-ΔP7 and pD29-ΔP11 (FIG. 1) were obtained. These clones have the respective deletions in the P protein and the R to D substitution in the G protein.

Recovery and propagation of recombinant viruses: Approximately $1.5 \times 10^6$ BSR T7 cells (Buchholz et al., 1999, J. Virol. Vol. 73, pp. 251–259) were transfected with a plasmid mixture containing 5 µg of pT7T-N, 2.5 µg of pT7T-P, 2.5 µg of pT7T-L and with 10 µg of one of the full length plasmids using the Stratgene mammalian transfection kit ($CaPO_4$ protocol). Supernatants from transfected cells were passaged and infection of cells was monitored by direct immunofluorescence with an anti-RV nucleoprotein conjugate (Centocor). The recombinant viruses were further passaged for 2 to 3 times and the resulting virus stocks were titrated by end point dilutions.

Replication of recombinant viruses in vitro: To compare the efficiency of virus production under multiple cycles of infection, BSR T7 cells were infected with a multiplicity of infection (m.o.i.) of 0.02. Supernatants were harvested two days after infection and titrated by end-point dilutions. For one-step growth curve analysis, $10^6$ BSR-T7/5 cells were grown in 3.2-cm-diameter dishes overnight and infected in duplicates with a multiplicity of infection (MOI) of 10 with the various recombinant viruses. After 2 h of incubation at 37° C., the inoculum was removed and the cells were rinsed three times with PBS. Cells were supplied with 2.5 ml of fresh medium and further incubated at 37° C. At 4, 18, 24 and 48 h after infection 100 µl of culture supernatants were removed and titered in duplicate on BSR- T7/5 cells.

RT-PCR and Sequence analysis: To determine whether the recombinant viruses maintain the introduced deletions, total RNA was isolated from BSR cells infected with passage level four of the respective stock viruses. RT-PCR was performed on 1 µg of total RNA isolated from infected cells. The PCR products were analysed on 1% agarose gels and used directly for sequencing.

Protein composition of mutant viruses. To analyze the protein composition of recombinant viruses, ~$10^7$ BSR-T7/5 cells were infected at an MOI of 0.02 and incubated for 2 days. Virions in the supernatant were then purified and concentrated by centrifugation through a 20% sucrose cushion in a Beckman SW28 rotor at 25,000 rpm for 90 min. Pellets were resuspended and mixed with protein sample buffer to disrupt the virions. Viral proteins from purified virions were then resolved by sodium-dodecyl-sulfate-polyacrylamide gel electrophoresis (SDS-PAGE) and transferred to PVDF membranes (Millipore). After incubation with a blocking solution, membranes were incubated with rabbit serum raised against RV ribonucleoprotein, S50 (Mebatsion, et al. Cell 84. pp. 941–951, 1996) or a rabbit polyclonal anti-LC8 antibody, R4058 (King, S. M., and R. S. Patel-King. J. Biol. Chem. 270 pp. 11445–11452, 1995). Membranes were then incubated with peroxidase-conjugated goat anti-rabbit immunoglobulin-G. Proteins were visualized after incubation with peroxidase substrate (Vector).

Mice inoculation Groups of each six 1–2 day-old suckling Balb/c mice were inoculated intramuscularly (i.m.) or intracranially (i.c) with a volume of 0.03 ml of virus suspensions at various concentrations. Mice were observed for rabies symptoms for a total of 21 days. A 20% brain suspension was prepared from dead mice and virus isolation was done in cell culture. The lethal dose that kills 50% of the animals ($LD_{50}$) was calculated using the method of Reed and Muench.

Table 1 Sequence of primer pairs used to introduce deletions into rabies virus P gene (strain SAD-B19)

TABLE 1

| Primers pairs | Sequence in 5'–3' orientation | Position of deleted nucleotides or amino acids |
|---|---|---|
| #142 | CGA AAG TCT TCA GAG GGC CGA GAG CTC AAG (SEQ ID NO. 1) | 1940 to 1960 (amino acids 143 to 149 of P protein) |
| #143 | CTT GAG CTC TCG GCC CTC TGA AGA CTT TCC (SEQ ID NO. 2) | |
| #144 | CCC AAC CCT CCA GGA GGC CGA GAG CTC AAG (SEQ ID NO. 3) | 1928 to 1960 (amino acids 139 to 149 of P protein) |
| #145 | CTT GAG CTC TCG GCC TCC TGG AGG GTT GGG (SEQ ID NO. 4) | |

Results

Safety of live oral rabies vaccines is a primary concern of public health. Rabies virus mutants having modification at the Arg 333 position of the glycoprotein are the most attenuated strains currently available. However, these strains are still pathogenic for suckling mice at 1–2 days of age, demonstrating the potential danger of such live vaccines for immunocompromised animals or humans. Therefore, a more safe strain is greatly needed for immunization against rabies using live vaccines.

Figure 2:
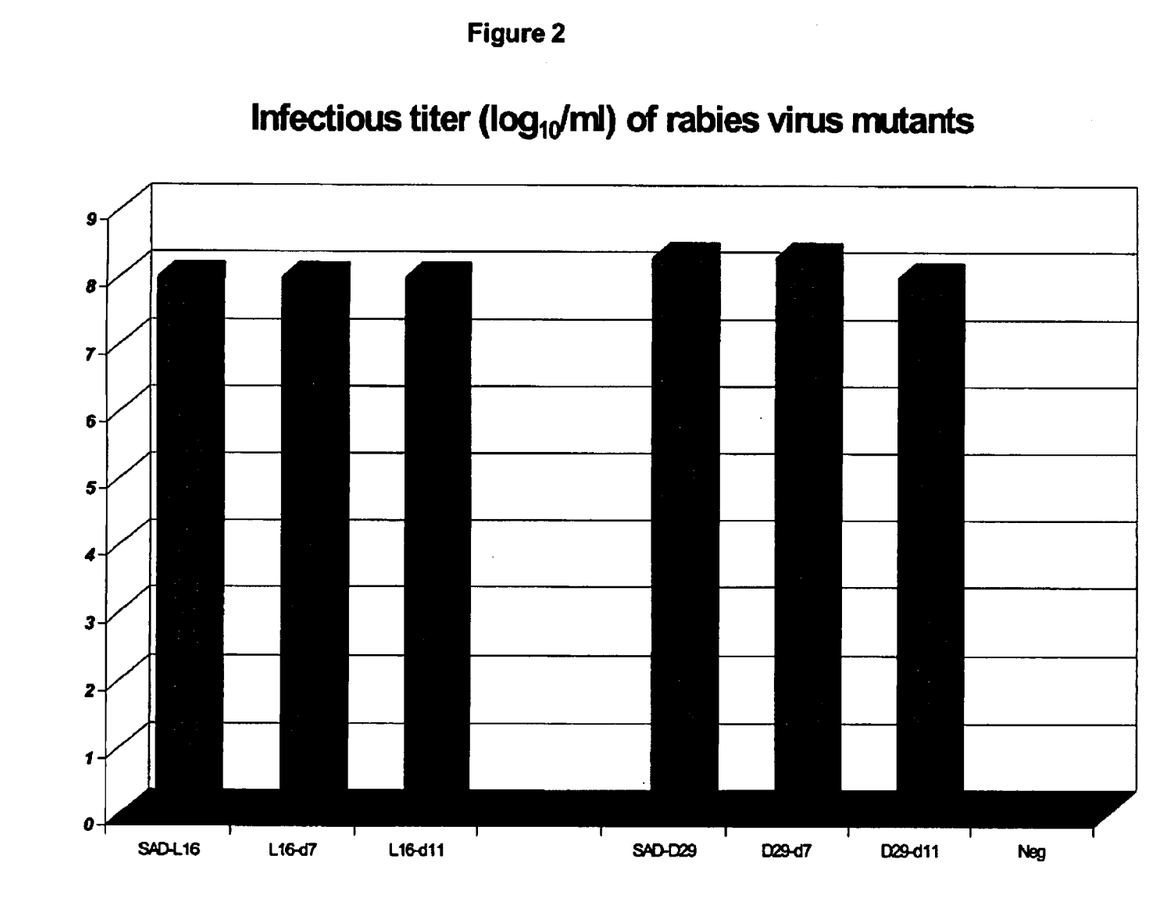
FIG. 2. Infectious titers of recombinant rabies virus mutants. BSR cells were infected at a m.o.i. of 0.02 and incubated for 2 days. Supernatants were harvested and titrated by end-point dilution. Titers were expressed in focus forming units (ffu) $\log_{10}$/ml. -d7 and -d11 represents -ΔP7 and -ΔP11, respectively.
Figure 3:
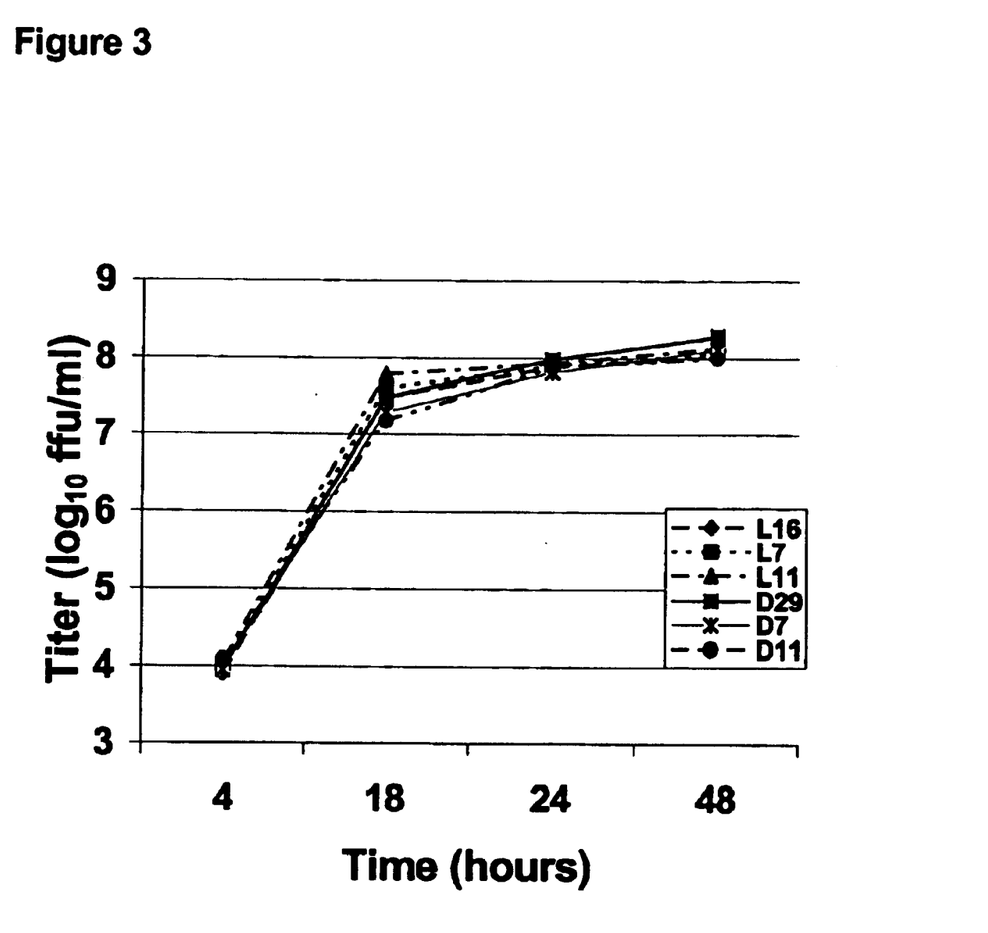
FIG. 3. One-step growth curves of recombinant RVs. BSR-T7/5 cells were infected with the recombinant RVs SAD-L16 (L16), L16-ΔP7 (L7), L16-ΔP11 (L11), SAD-D29 (D29), D29-ΔP7 (D7), and D29-ΔP11 (D11) at an MOI of 10. Aliquots of cell culture supernatants were collected at the indicated time points and viral titers were determined in duplicates by serial dilutions. Titers were expressed in focus forming units (ffu) $\log_{10}$/ml.

The phosphoprotein (P) of rabies virus was shown to interact with a cytoplasmic LC8 dynein light chain. The LC8 binding domain was mapped to the central part of P (residues 138 to 172). It is suggested that the interaction between P and LC8 might be involved in rabies virus pathogenesis. Rabies virus mutants containing deletions of 7 (amino acids 143 to 149) or 11 residues (amino acids 139 to 149) in the LC8 binding domain of the P protein were constructed. All mutants were successfully recovered in cell cultures. Titers identical to that of the parent virus were obtained for all mutant viruses (FIG. 2) and all the mutants propagated in cell culture as efficiently as the parent strains at different time points (FIG. 3).

Figure 4:
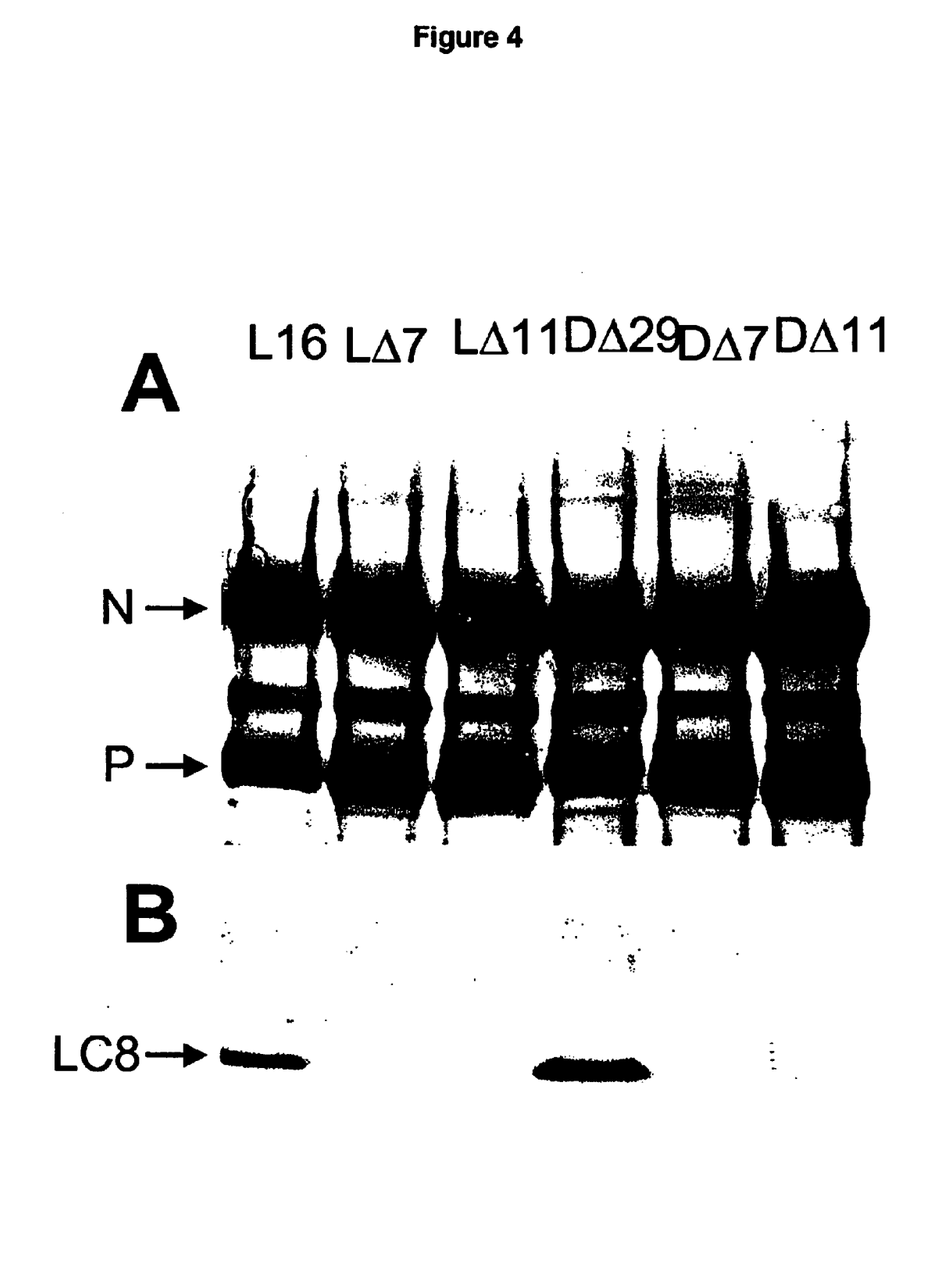

To determine the expression level of mutant P proteins and to elucidate the association between P protein and LC8, proteins from purified viruses were analyzed by Western immunoblotting. The blots were incubated with an anti-RV RNP rabbit serum (S50) or an anti-LC8 polyclonal antibody (R4058). The amounts of P proteins or the ratios between P and N proteins of the mutant viruses were indistinguishable from that of the parent viruses, indicating that the deletions of 7 or 11 amino acids from the LC8 binding site have no influence upon expression of mutated P proteins. In contrast to the respective parent viruses, no protein corresponding to LC8 could be detected in mutant viruses with deletion at the LC8 binding site (FIG. 4). This result demonstrates that incorporation of LC8 into virions membrane is driven by a specific interaction between P and LC8 and the introduced deletions were sufficient to entirely block the association between P protein and LC8.

Figure 5:
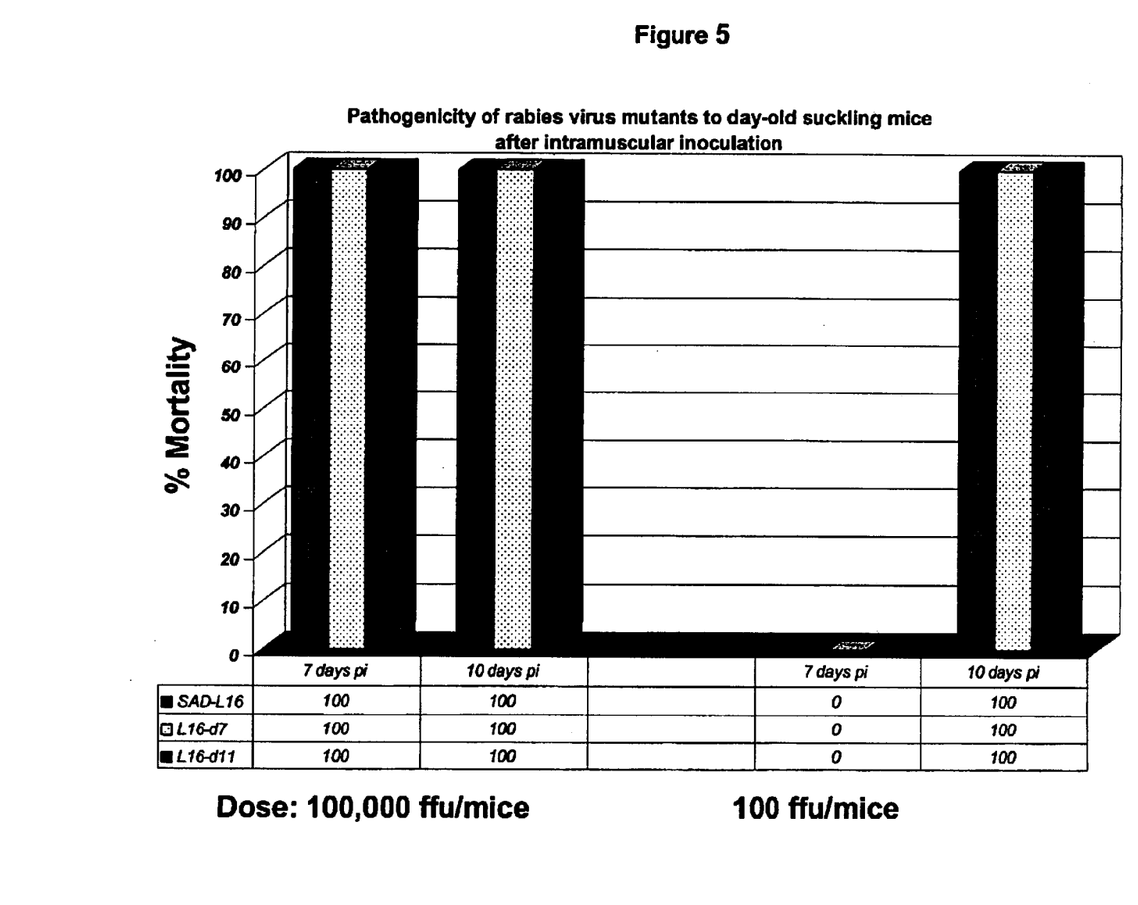
FIG. 5. Pathogenicity of rabies virus mutants, strain SAD-L16, L16-ΔP7 (L16-d7), and L16-ΔP11 (L16-d11) to day-old suckling mice. Suckling mice were inoculated with doses of 100 ffu/mouse or 100,000 ffu/mouse intramuscularly and observed daily for a total of 21 days. Results recorded at the end of 7 and 10 days were presented. All animals in all three groups were died of rabies within 10 days after inoculation.

To compare the pathogenicity of the mutants derived from SAD-L16, 1–2 day-old suckling mice were inoculated intramuscularly with the parent virus or with one of the deletion mutants (L16-ΔP7 or L16-ΔP11) at a dose of 100 or 100,000 ffu/mouse. As shown in FIG. 5, all suckling mice inoculated with 100,000 ffu/mouse were died of rabies within 7 days of inoculation. Mice in all groups inoculated with 100 ffu/mice were died of rabies within 10 days of inoculation (FIG. 5), indicating that deletion of 7 or 11 residues from the LC8 binding site of the P protein does not significantly decrease the pathogenicity of rabies virus for suckling mice.

Figure 1:
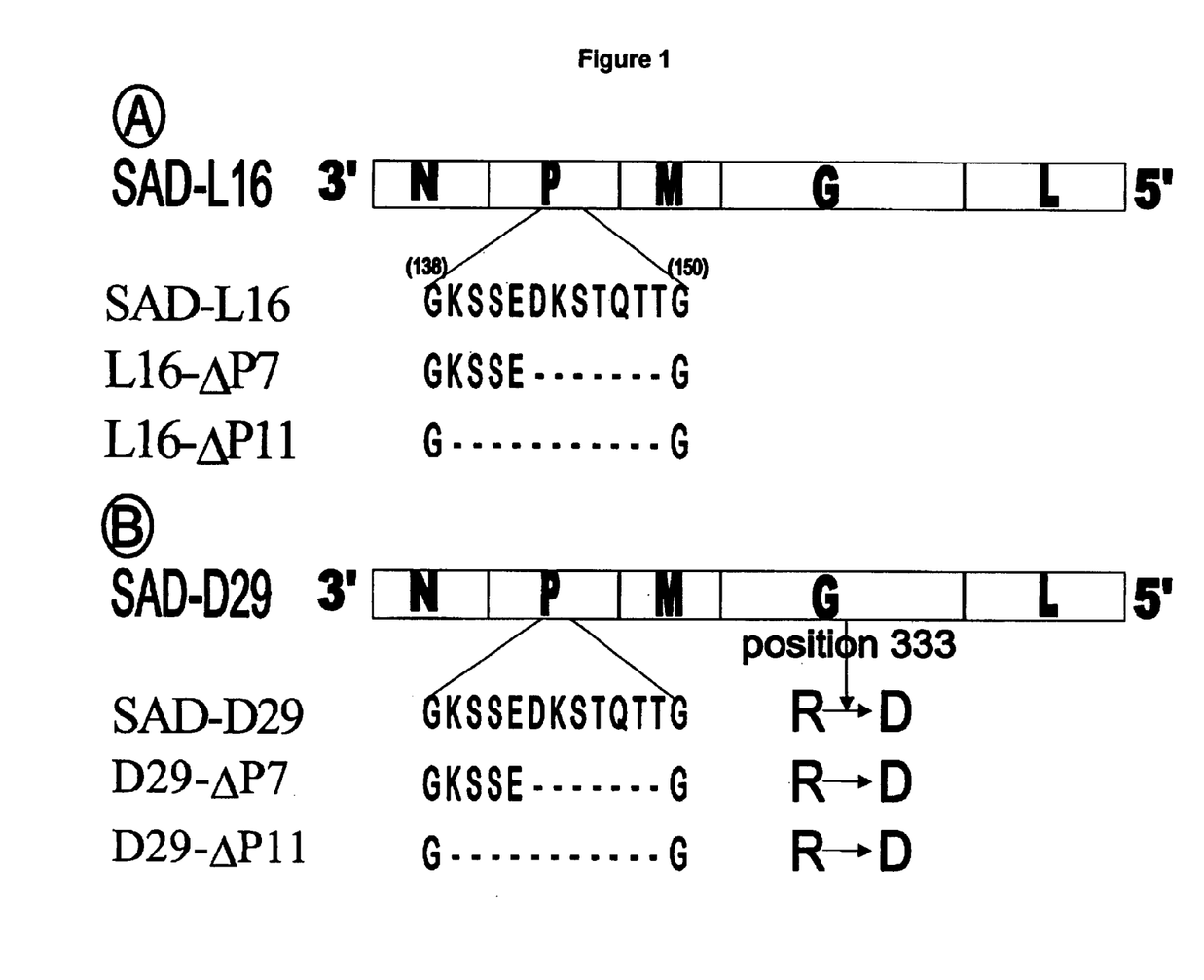
FIG. 1. A schematic representation of the rabies virus gene order in the negative-strand genomic RNA. (A) Gene order of SAD-L16, a recombinant rabies virus possessing the authentic sequence of SAD-B19 (Conzelmann et al. 1990, Virology, Vol. 175, pp. 485–499). (B) Gene order of SAD-D29, a recombinant rabies virus possessing an Arg (R) to Asp (D) substitution at position 333 of the G protein of SAD-B19. Amino acid sequence (positions 138 to 150) around the LC8 dynein light chain binding site of the phosphoprotein (P protein) is shown. ΔP7 or ΔP11 are mutants with the indicated deletions of 7 or 11 amino acids at the LC8 binding site of the P protein.
Figure 6:
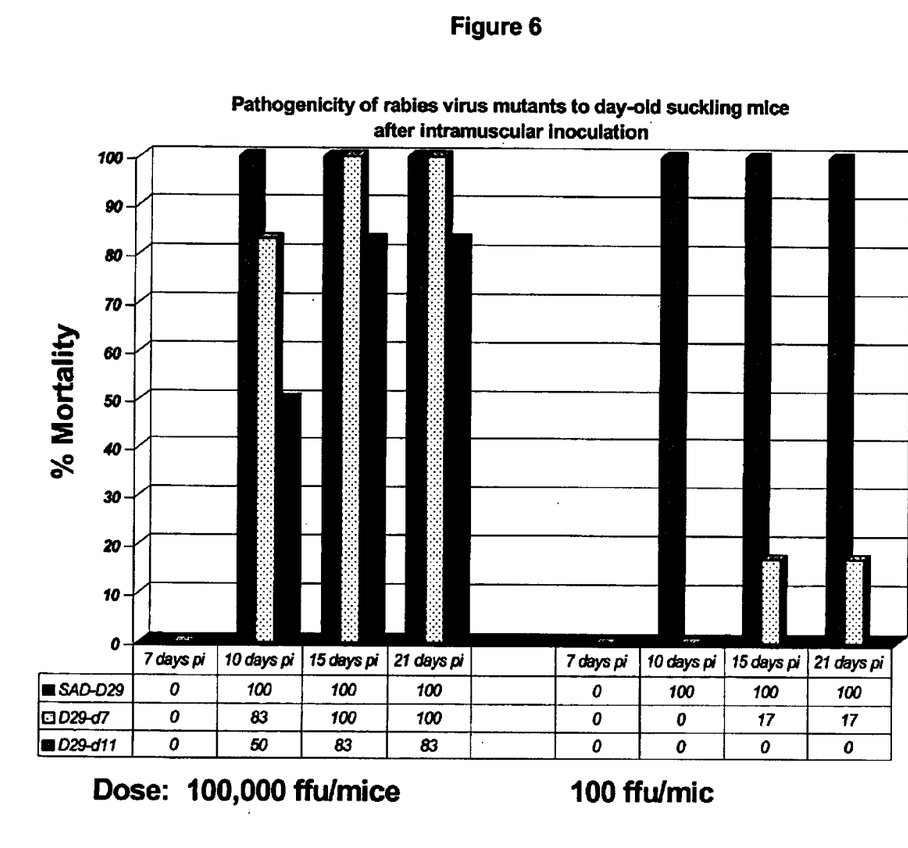
FIG. 6. Pathogenicity of rabies virus mutants, strain SAD-D29, D29-ΔP7 (D29-d7), and D29-ΔP11 (D29-d11) to day-old suckling mice. Suckling mice were inoculated with doses of 100 ffu/mouse or 100,000 ffu/mouse intramuscularly and observed daily for a total of 21 days. Results recorded at the end of 7, 10, 15, and 21 days were presented. No mortality has occurred in the group of mice that were inoculated with 100 ffu/mouse of D29-ΔP11 (D29-d11).

Mutants containing identical deletion of 7 or 11 amino acids in their P protein as well as an Arg (R) to Asp (D) substitution at position 333 of their G protein were then generated (FIG. 1). These mutants (D29-ΔP7 and D29-ΔP11) grew in cell culture to similar titer to that of SAD-D29, which contains only the R to D substitution (FIG. 2 and 3). To compare the pathogenicity of the combined mutants with that of the single mutant, 1–2 day-old suckling mice were inoculated intramuscularly at a dose of 100 or 100,000 ffu/mouse. Within 10 days post-inoculation, all mice inoculated with both doses of SAD-D29 were died of rabies. In contrast, only 83% or 50% of the mice that have received a dose of 100,000 ffu/mouse of D29-ΔP7 or D29-ΔP11, respectively, have died of rabies 10 days after infection. Fifteen days after infection, the mortality reached 100% and 83%, respectively, and remained the same until the end of the 21 days observation period (FIG. 6).

Surprisingly, no mortality has occurred in the groups of mice inoculated with D29-ΔP7 or D29-ΔP11 at a dose of 100 ffu/mouse by the end of 10 days after infection. Until the end of the 21 days observation period no mortality has occurred in the group of D29-ΔP11 inoculated mice, whereas in the group of mice that were inoculated with D29-ΔP7 there was less than 17% (one out of six) mortality (FIG. 6). These unexpected results demonstrate that the combination of LC8 binding site mutation and the amino acid change at Arg333 of the G protein considerably attenuates rabies virus virulence for suckling mice.

Figure 7:
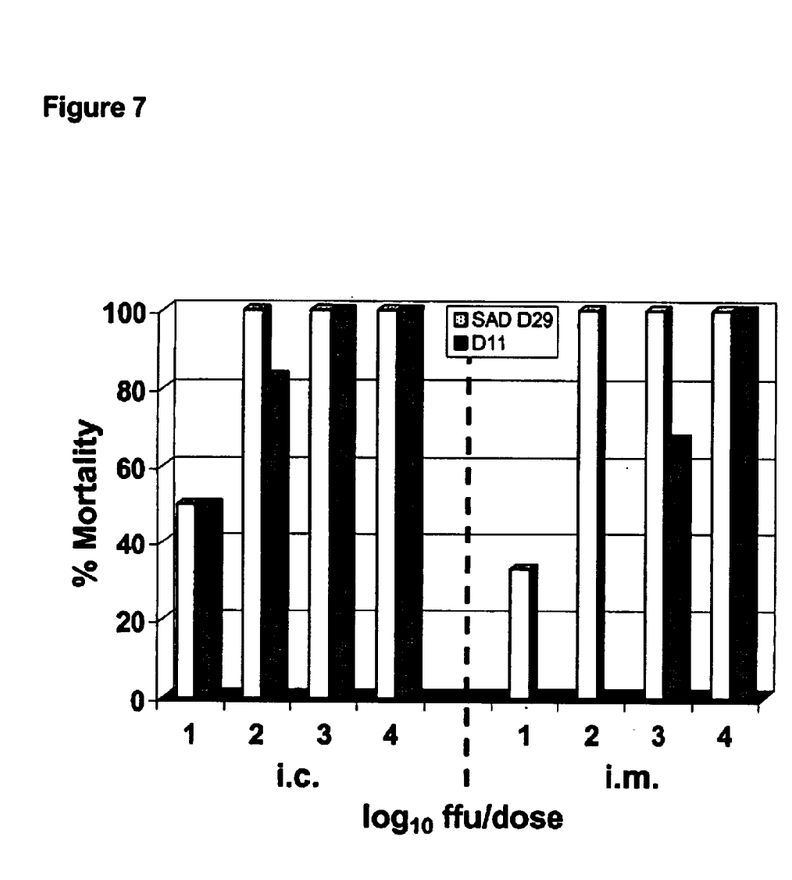
FIG. 7. Comparison of the degree of pathogenicity of recombinant RVs after intracranial (i.c.) or intramuscular (i.m.) inoculations. Two-days-old suckling mice were inoculated with SAD-D29 (D29) or D29-ΔP11 (D11) by i.c. or i.m. route at the indicated doses. After i.c. inoculation, the LD50 of SAD-D29 and D29-ΔP11 were 10 and 14 ffu/30 μl, respectively. Whereas after i.m. inoculation, the $LD_{50}$ of D29-ΔP11 was 556 ffu as opposed to only 18 ffu for SAD-D29, indicating that D29-ΔP11 is attenuated by as much as 30-fold.

Next, the degree of attenuation of the recombinant D29-ΔP11 was analyzed by administering graded doses into 1-to 2-day-old suckling mice by i.m. or i.c. routes. As shown in FIG. 7, the dose of D29-ΔP11 that was required to kill 50% ($LD_{50}$ per 30 μl) of the i.m. inoculated 2-day-old suckling mice was 556 ffu, whereas the $LD_{50}$ of the parent SAD-D29 virus was only 18 ffu. This demonstrates that D29-ΔP11 is attenuated by as much as 30-fold when administered by the i.m. route. Interestingly, a very similar $LD_{50}$ of 10 and 14 ffu was obtained for SAD-D29 and D29-ΔP11, respectively, when the strains were administered by i.c. routes (FIG. 7). This remarkable attenuation after i.m., but not after i.c. administration shows that D29-ΔP11 spreads inefficiently from a peripheral site of infection to the CNS, compared to the parent virus. These results demonstrate that elimination of the LC8 ligand and simultaneous substitution of R333 considerably attenuates RV pathogenicity after peripheral inoculation and may be helpful in designing and developing highly safe live RV based vaccines.

Example 2

Safety and Efficacy of Recombinant rabies Viruses in Dogs After oral Administration Materials and Methods To determine the safety and efficacy of the recombinant viruses after oral administration, three- to four-months-old rabies seronegative dogs were divided into three groups of 4 dogs each. Group 1 and 2 received a dose of $10^8$ focus forming units (ffu) in a volume of 2 ml of SAD-D29 or D29-ΔP11, respectively, by oral instillation. Group 3 served as a control. Saliva swabs were taken on days 1, 3 and 7 after vaccination to test for vaccine virus excretion by inoculating into cell cultures. Blood samples from all animals were taken before vaccination, 2 and 8 weeks after the first immunization. Groups 1 and 2 were boosted with similar doses of the respective vaccines 8 weeks after the first immunization. Blood samples were again collected 2 weeks after the booster immunization. Serum samples were heat inactivated for 30 minutes at +56° C. and stored at −20° C. until use. The absence/presence of antibodies against rabies was determined by rapid fluorescent focus inhibition test (RFFIT) as described in "WHO Laboratory Techniques in Rabies" (1996). Throughout the experiment the dogs were observed daily for general health conditions.

Results

Figure 8:
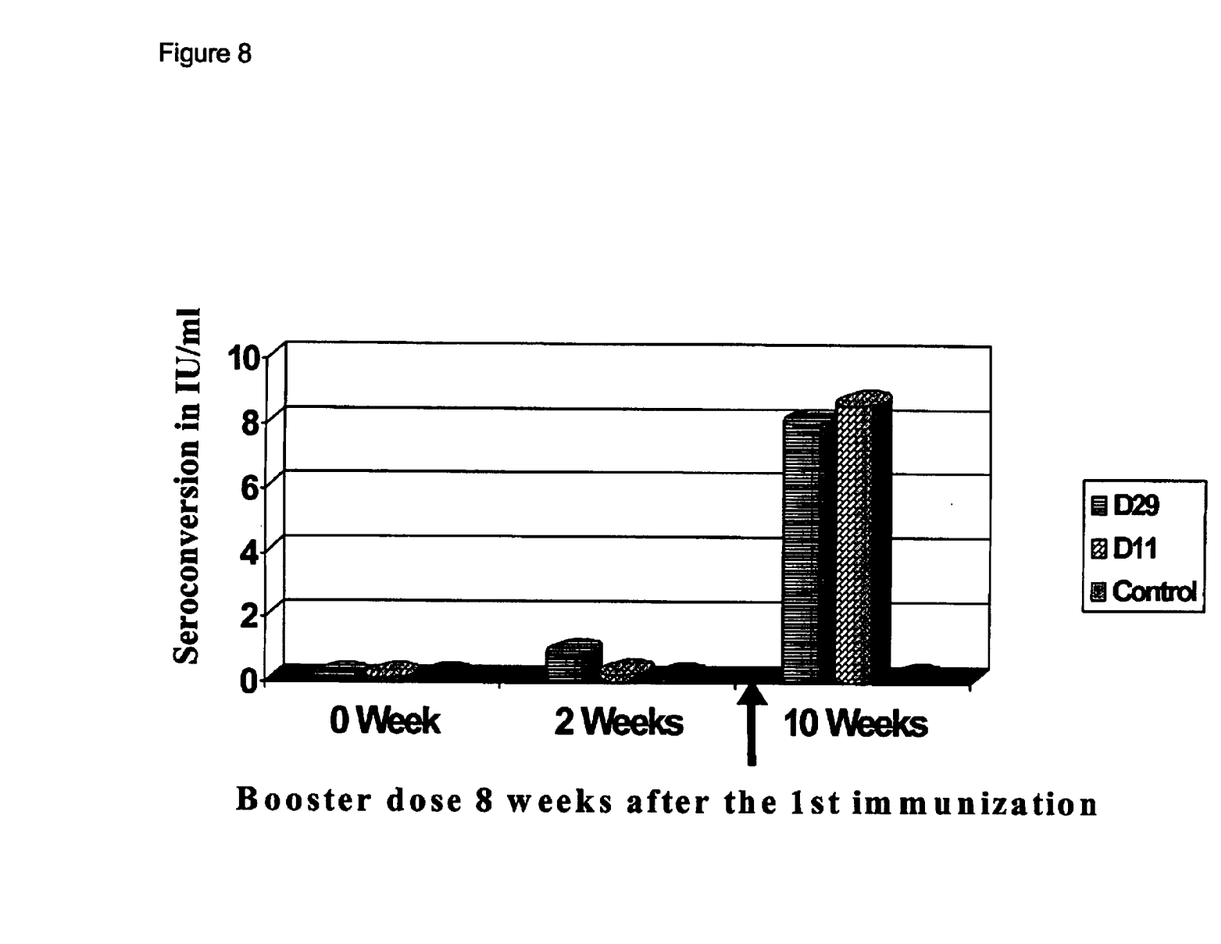
FIG. 8. Immunogenicity of recombinant rabies virus vaccines after oral administration. Three- to four-months-old rabies seronegative dogs were divided into three groups of 4 dogs each. Group 1 (D29) and 2 (D11) received a dose of $10^8$ focus forming units (ffu) in a volume of 2 ml of SAD-D29 or D29-ΔP11, respectively, by oral instillation. Group 3 served as a control. Groups 1 and 2 were boosted with similar doses of the respective vaccines 8 weeks after the first immunization. Rabies-specific antibody titers were determined by rapid fluorescent focus inhibition test (RFFIT) at the indicated time points.

All dogs remained clinically healthy throughout the observation period of 3 months. All saliva swabs collected at different time points tested negative for the presence of the vaccine viruses, indicating absence of virus excretion at the indicated times. To determine the effect of the 11 amino acids deletion in the P protein upon the immunogenicity of the virus, dogs were immunized with SAD-D29 or D29-ΔP11 by oral instillation. Two weeks after the first immunization the rabies-specific titers in both groups of animals did not differ significantly (FIG. 8). Since administration of rabies vaccines by oral route is less effective than parenteral administration, a booster dose was given 8 weeks after the first immunization. As shown in FIG. 8, there was a dramatic comparable increase in rabies-specific antibody titers in both groups of animals immunized either with SAD-D29 or D29-ΔP11. These results demonstrate that deletion of as much as 11 amino acids from the LC8 binding site of rabies virus P protein did not affect immunogenicity of the virus when administered by oral route into dogs.

BRIEF DESCRIPTION OF THE FIGURES

FIG. 4. Protein composition of recombinant RVs. Approximately $10^7$ BSR-T7/5 cells were infected with the recombinant RVs SAD-L16 (L16), L16-ΔP7 (LΔ7), L16-ΔP11 (LΔ11), SAD-D29 (D29), D29-ΔP7 (DΔ7), and D29-ΔP11 (DΔ11) at an MOI of 0.02. Two days after infection, virions from supernatants were purified over 20% sucrose cushion and viral pellets were analyzed by Western blotting. Using a protein marker as an indicator the same blot was cut into two parts at approximately ~20 kD position. The upper part of the blot was incubated with anti-RV RNP serum (A) and the lower part of the blot was incubated with a rabbit polyclonal LC8 antibody (B). Incorporation of LC8 could be detected only in the parent viruses SAD-L16 and SAD-D29, but not in the recombinant viruses possessing deletions at the LC8 binding site.

What is claimed is:

1. A recombinant rabies virus mutant comprising a mutation in the G protein and a mutation in the P protein, which mutation in the P protein is a deletion comprising the amino acids at positions 143 to 149.

2. A mutant according to claim 1 wherein the mutation in the P protein is a deletion selected from the group consisting of amino acids 143 to 149 and 139 to 149.

3. A mutant according to claim 1 wherein the mutation in the P protein is a deletion of amino acids 139 to 149.

4. A mutant according to claim 1 wherein the mutation in the G protein is an amino acid substitution of the arginine at position 333 for another amino acid.

5. A mutant according to claim 4 wherein the $Arg_{333}$ is replaced with Asp.

6. A mutant according to claim 4, wherein the $Arg_{333}$ codon is replaced with GAC.

7. A mutant according to claim 1 wherein the mutation in the G protein is a replacement of the $Arg_{333}$ codon with GAC and wherein the mutation in the P protein is a deletion of amino acids 139 to 149.

8. A mutant according to claim 1 where said mutant is a mutant of RV strain SAD Bern or SAD B19.

9. A recombinant rabies virus according to claim 1 additionally expressing a nucleic acid encoding a heterologous antigen.

10. A recombinant rabies virus according to claim 9 wherein the said antigen derived from human or animal pathogen.

11. A recombinant rabies virus according to claim 9 additionally expressing a gene encoding an immune-stimulatory protein.

12. A vaccine comprising a mutant according to claim 1.

13. The vaccine of claim 12 wherein the—mutant comprises a mutation in the G protein wherein the—$Arg_{333}$ codon is replaced with GAC and wherein the mutation in the P protein is a deletion of amino acids 139–149.

14. The vaccine of claim 12 wherein the mutation comprises a mutation in the P protein which encompasses one or more of the amino acids at positions 143 to 149 and 139 to 149.

15. The vaccine of claim 12 wherein the—mutant comprises a—mutation in the G protein—wherein—the arginine at position 333—is substituted—for another amino acid.

16. The vaccine of claim 12 wherein the—mutant comprises a mutation in the G protein wherein the—$Arg_{333}$ codon is replaced with GAC or the $Arg_{333}$ codon is replaced with Asp.

17. The vaccine of claim 12 wherein said mutant is a mutant selected from the group consisting of RV strain SAD Bern and SAD B19.

18. A recombinant rabies virus mutant comprising a mutation in the G protein and a mutation one or more of the amino acids at positions 143 to 149 and 139 to 149 in the P protein.

* * * * *